United States Patent
Pittman

[11] Patent Number: 6,053,314
[45] Date of Patent: *Apr. 25, 2000

[54] RECEPTACLE FOR CONTAMINATED WASTES

[75] Inventor: William G. Pittman, Knoxville, Tenn.

[73] Assignee: DeRoyal Industries, Inc., Powell, Tenn.

[*] Notice: This patent issued on a continued prosecution application filed under 37 CFR 1.53(d), and is subject to the twenty year patent term provisions of 35 U.S.C. 154(a)(2).

[21] Appl. No.: 09/095,282

[22] Filed: Jun. 10, 1998

[51] Int. Cl.[7] .................................................. B65D 83/10
[52] U.S. Cl. ............................................ 206/366; 206/370
[58] Field of Search ................................... 206/438, 63.5, 206/363–366, 370; 220/908–910; 588/249, 258

[56] References Cited

U.S. PATENT DOCUMENTS

| | | | |
|---|---|---|---|
| 4,816,307 | 3/1989 | Honeycutt | 206/366 |
| 4,874,103 | 10/1989 | Quisenberry et al. | 206/366 |
| 4,936,449 | 6/1990 | Conrad et al. | 206/366 |
| 5,187,850 | 2/1993 | McCammon et al. | 206/366 |
| 5,323,902 | 6/1994 | Palmer et al. | 206/366 |
| 5,409,112 | 4/1995 | Sagstetter | 206/366 |
| 5,409,113 | 4/1995 | Richardson et al. | 206/366 |
| 5,707,173 | 1/1998 | Cottone et al. | 206/366 |
| 5,758,775 | 6/1998 | Lowe | 206/364 |

*Primary Examiner*—Paul T. Sewell
*Assistant Examiner*—Luan K. Bui
*Attorney, Agent, or Firm*—Pitts & Brittian P

[57] ABSTRACT

A receptacle for liquid medical wastes including an open top vessel having a bottom, an integral upstanding wall (or multiple side walls in one embodiment) defining an upper flanged rim, a lid adapted to cover the open top of the vessel in sealing engagement with the flanged rim, a recess defined preferably centrally of the lid and including an opening through the lid which is disposed centrally of the recess, a closure flap anchored at one of its ends to the top surface of the lid at a spaced apart location relative to the recess and being adhesively attachable to the top surface of the lid and in covering relationship to the recess, and means for releasably anchoring the receptacle during its use in a theater of medical operation. The receptacle is formed from incineratable material, such as recycled plastic materials. In one embodiment, the vessel contains liquid absorptive material (s).

10 Claims, 5 Drawing Sheets

RECEPTACLE FOR CONTAMINATED WASTES

BACKGROUND OF INVENTION

This invention relates to receptacles for contaminated wastes, particularly contaminated liquid medical wastes.

Receptacles for contaminated liquid medical wastes desirably are unobtrusively positioned, yet readily accessible, within the theater of operations for a given medical procedure. They further preferably are releasably anchored during the time period when liquid medical wastes are to be introduced into the receptacle, are adapted for easy and certain introduction of the wastes into the receptacle without fear of inadvertent dispersal of contaminated liquid waste into the theater of operation of the medical personnel, are provided with means for leak-proof closure for disposal, are fully incineratable for disposal without escape of the wastes from the container, and are relatively inexpensive to manufacture. Known prior art receptacles fail to provide one or more of these desirable features. One of the more important failures of the prior art receptacles for liquid medical wastes relates to the function of introduction of the liquid waste into the receptacle. In this respect, it is noted that in most medical procedures, there is a degree of urgency to complete the treatment, almost irrespective of the nature of the injury or medical condition being treated. This factor leads to hurried movements, and disposal of liquid medical waste presents one of the more problematic aspects of safety to the medical personnel and/or the patient. More specifically, much of the liquid medical waste generated during a medical procedure is collected or accumulated in a syringe, and in some instances the same syringe is used to collect multiple volumes of liquid from a patient. Emptying the liquid from the syringe between collections is by necessity to be accomplished quickly. This factor can lead to splatter of liquid being expelled from the syringe, either from the syringe not being properly inserted into a receptacle for the liquid or splatter from the receptacle itself.

After the receptacle is filled to its capacity with liquid waste, it becomes necessary that the receptacle be sealed fluid-tight for removal from the theater of operations and subsequent disposal. Recalling that desirably the receptacle is nonobtrusive to the activities of the medical personnel, to this end liquid waste receptacles are designed to be relatively small. In this regard, it is not uncommon that more than one receptacle is required to contain the volume of liquid waste from a given procedure, thereby making it important that the sealing of the filled receptacle not only be certain, but that it be accomplished with a minimum of effort and in the shortest time possible.

It is therefore an object of the present invention to provide a receptacle for liquid medical wastes which is inexpensive to manufacture and which provides for ready receipt therein of the liquid wastes and ultimate safe disposal of the waste-containing receptacle.

It is another object of the present invention to provide a receptacle for liquid medical wastes which minimizes the likelihood of splatter of the liquid wastes in the course of introduction of the liquid waste into the receptacle and during subsequent handling of the receptacle.

BRIEF DESCRIPTION OF DRAWINGS

Other objects and advantages of the present invention will be recognized for the description contained herein, including the claims and the Figures in which:

SUMMARY OF INVENTION

The present invention comprises a receptacle for liquid medical wastes and includes an open top vessel having a bottom, an integral upstanding wall (or multiple side walls in one embodiment) defining an upper flanged rim, a lid adapted to cover the open top of the vessel in sealing engagement with the flanged rim, a recess defined preferably centrally of the lid and including an opening through the lid which is disposed centrally of the recess, a closure flap anchored at one of its ends to the top surface of the lid at a spaced apart location relative to the recess and being adhesively attachable to the top surface of the lid and in covering relationship to the recess, and means for releasably anchoring the receptacle during its use in a theater of medical operation. The receptacle is formed from incineratable material, such as recycled plastic materials. In one embodiment, the vessel contains liquid absorptive material(s).

DETAILED DESCRIPTION OF INVENTION

Figure 1:
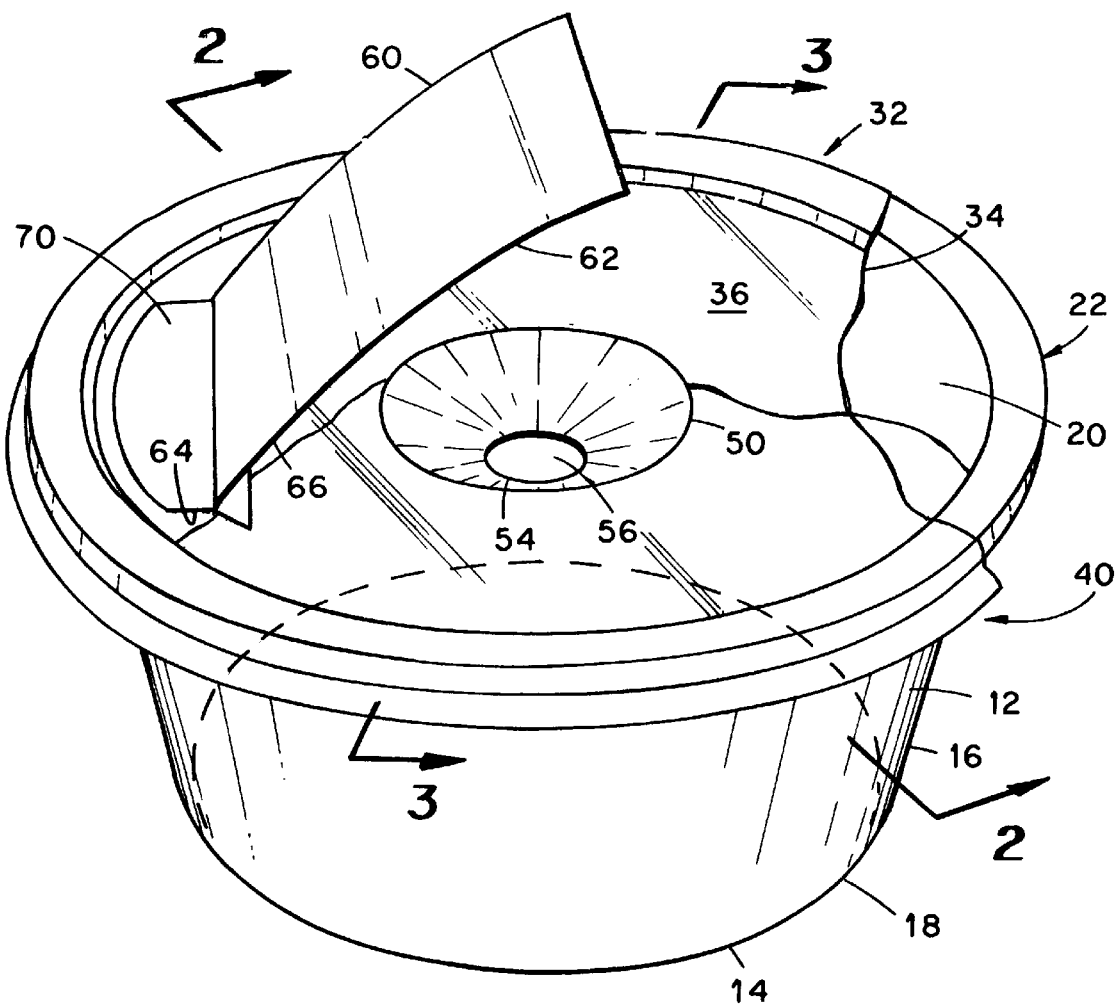
FIG. 1 is a perspective view of one embodiment of a receptacle embodying various of the features of the present invention.
Figure 2:
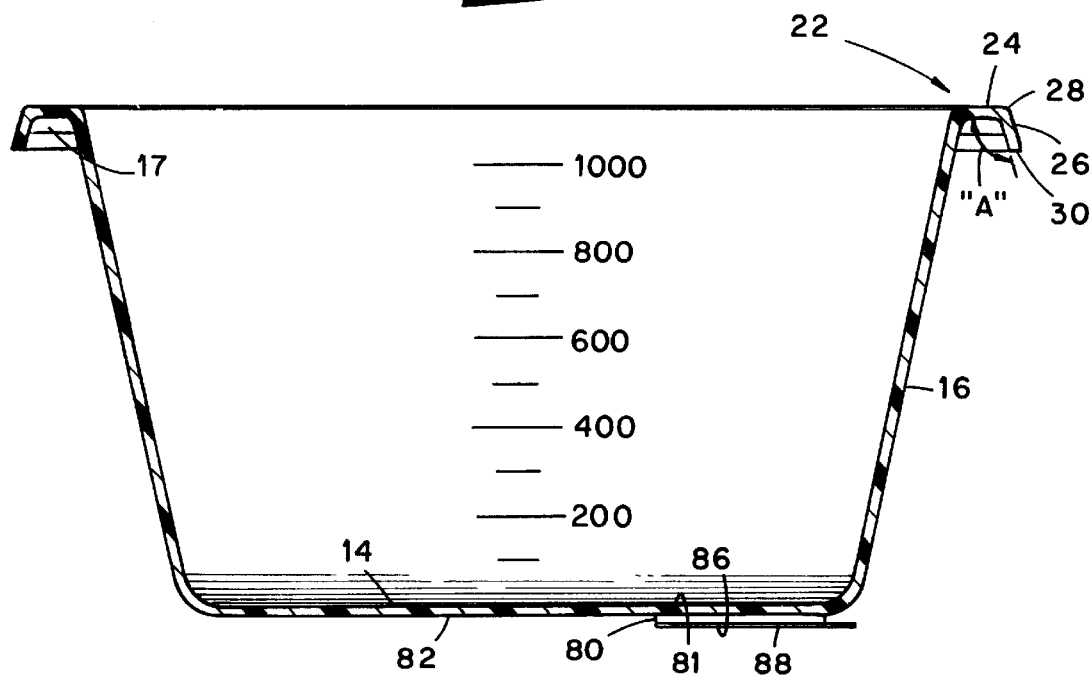
FIG. 2 is a side elevation view, in section, of the receptacle of FIG. 1 and taken generally along the line 2—2 of FIG. 1.
Figure 5:
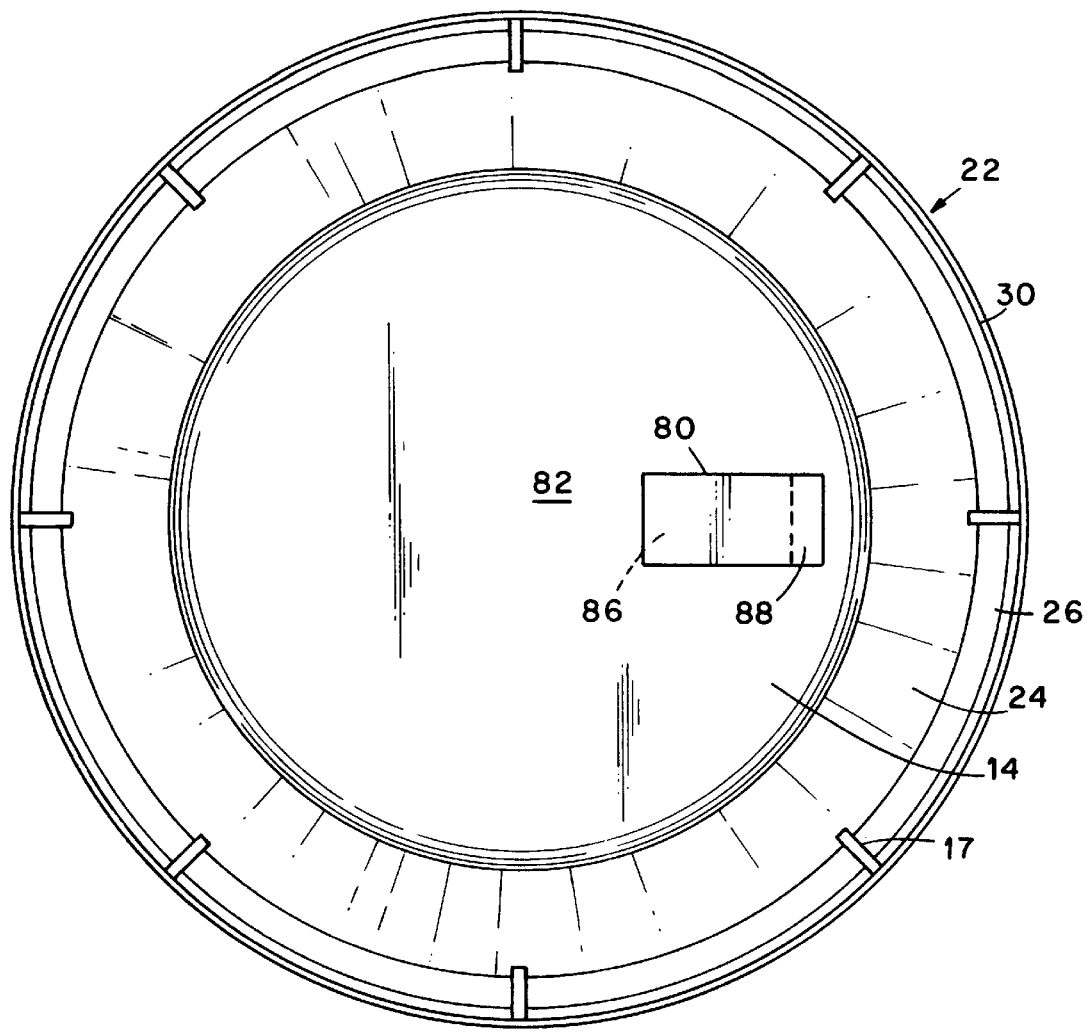
FIG. 5 is a bottom view of the receptacle of FIG. 1 and depicting means for releasably anchoring the receptacle during use; and, FIG. 6 is a perspective view of a further embodiment of a receptacle of the present invention.

In embodiment of the receptacle of the present invention depicted in FIG. 1, there is provided a vessel 12 which includes a bottom 14, which is circular in the depicted embodiment and preferably substantially planar, and a wall 16 which is integrally formed with the outer circumferential margin 18 of the bottom and upstanding therefrom to define an open top 20 having an outer circumferential rim 22. In the depicted embodiment, the wall 16 flares outwardly and upwardly from the bottom 14 so that the circumference of the vessel at its open top is greater than its circumference adjacent the bottom 14. The depicted rim 22 includes a lateral flange portion 24 and a circumferential lip portion 26 which depends from the outer circumferential edge 28 of the flange portion. When viewed in cross section as in FIG. 2, this lip portion defines an obtuse angle "A" with the flange portion such that the lower circumferential edge 30 of the lip portion projects slightly outwardly from the vessel wall 16. As depicted in FIG. 5, as desired, gussets 17 may be provided between the wall 16 and the circumferential lip portion 26 to rigidify the lip portion 26.

The vessel 12 is provided with a lid 32 that includes a planar body portion 34 having a top surface 36 and a bottom surface 38 and which is bounded by a circumferential rim portion 40. This rim 40 includes a circumferential channel 42 that opens downwardly of the lid to receive therein the rim 22 of the vessel in sealing engagement therebetween when the lid is disposed in covering relationship to the open top of the vessel. In the depicted embodiment, the rim portion 40 of the lid includes a circumferential lip 44 disposed on the lower edge 46 of the outermost wall 48 of the channel 42 which is disposed in position to snap over the circumferential edge 30 of the lip portion of the flange portion of the top rim of the vessel 12 to thereby enhance the fluid-tight sealing engagement of the lid with the rim of the vessel.

Figure 3:
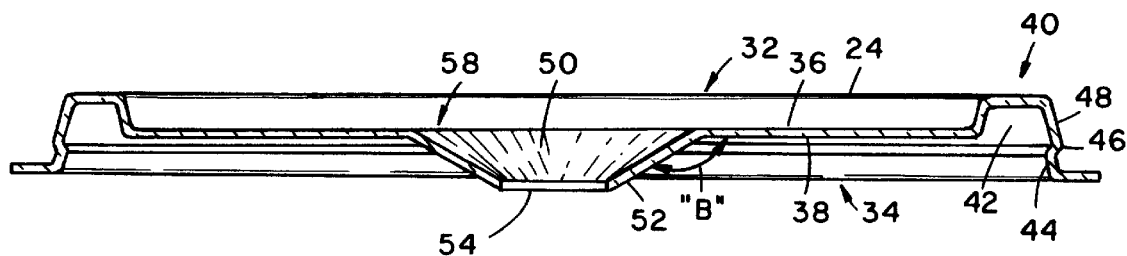
FIG. 3 is a side elevation view, in section, of the lid of the receptacle of FIG. 1 and taken generally along the line 3—3 of FIG. 1.

The body portion 34 of the lid 32, at a location preferably centrally thereof, is provided with a recess 50 which is frustroconical in cross-sectional geometry as depicted in FIGS. 1 and 3. The conical wall 52 of the recess, when viewed in cross section as in FIG. 3, defines an obtuse angle "B" with the planar body portion 34 of the lid. The bottom end 54 of the recess defines an opening 56 which communicates between the outside and inside of the vessel via the recess 50. This construction of the recess provides for the ready guidance of the needle-receiving end of a syringe, for example, toward the opening 56 so that such end of the syringe may be inserted into the opening for the expulsion of the contents of the syringe into the interior of the vessel 12. To this end, in one embodiment of a vessel of 1000 ml capacity, the major diameter 58 of the recess is about 52 mm and the diameter of the opening 56 is about 11 mm. The height of the recess from the opening 56 to the major diameter 58 thereof, in this embodiment is chosen to be about 12 mm, thereby creating an obtuse angle "B" of about 150 degrees. This construction of the recess is chosen for the purpose of reducing the likelihood of splatter of liquid from the interior of the vessel 12 out through the opening 56, during the course of addition of liquid waste into the vessel or when handling the vessel after it has been partially or fully filled with liquid waste. Contariwise to the known prior art containers for liquid medical wastes, the present invention provides both a guide for the user to locate the relatively small opening through the lid into the interior of the vessel, and acts as a type of shield against splatter of liquid from the interior of the vessel to the outside of the vessel through the opening 56. Preferably, this angle "B" is not less than about 140 degrees and does not exceed about 160 degrees. Wall angles "B" of less than about 140 degrees result in the recess wall being too steep to provide meaningful guidance toward the opening 56, whereas angles "B" of greater than about 160 degrees cause the recess to be too shallow for effective aid in guidance of a syringe tip into the opening 56 and/or shielding against splatter of liquid wastes from the vessel via the opening 56.

This feature of the present container is of particular importance when the container is employed for the receipt of liquid medical waste that is contained in a syringe. In this situation, the medical technician (e.g., doctor or nurse) desires to quickly empty the liquid contents of a syringe, either for the reason that they need to immediately reuse the syringe to collect further liquid, or they need to quickly dispose of the contents of the syringe so as to minimize the time span when their attention is diverted to the task of disposing of the liquid waste and away from the task of treating the patient. Under this circumstances, the present invention provides for ready guidance of the open end of the syringe into the opening 56, provides an opening of a size which accepts the open end of the syringe (sometimes known as the lure lock end of the syringe), and which does not exhibit sufficient open area for the splatter of liquid from the vessel during the course of the expulsion of liquid, under pressure, from the syringe or even after the syringe has been withdrawn from the opening.

In accordance with one aspect of the present invention, the interior of the vessel may be provided with absorptive material 60 for the liquid admitted to the vessel. In a preferred embodiment, this absorptive material may take the form of a plurality of layers of cellulose fibrous material or the like. As desired, a super absorbent material such as SANISORB® liquids absorber, from Multiform Dessiccants, Inc., of Buffalo, N.Y., may be added to the vessel to enhance the absorptive capacity of the vessel and/or to combine with the liquid to develop a gel-like material in the vessel.

Figure 4:
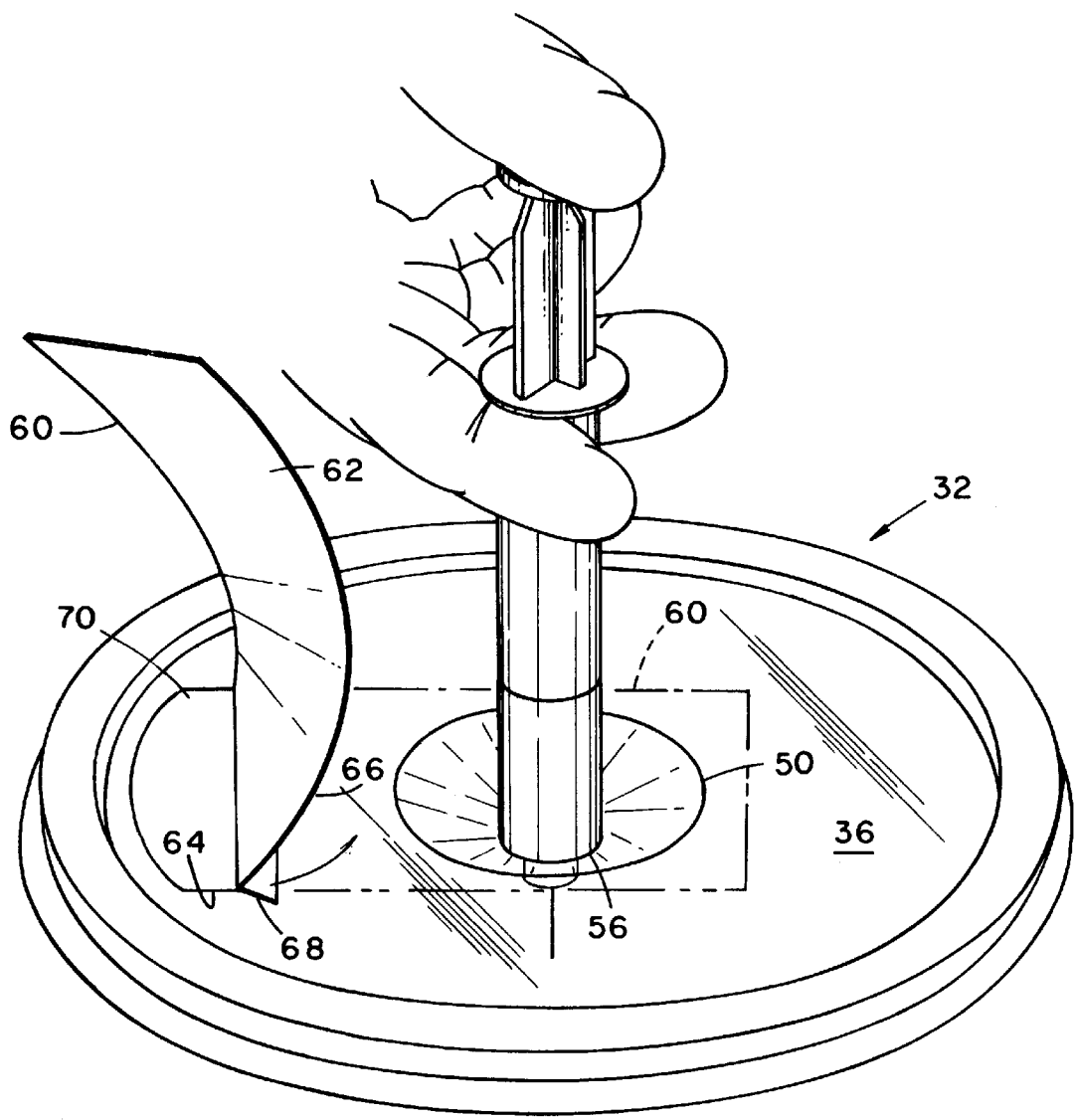
FIG. 4 is a representation of the lid of the receptacle of FIG. 1 and depicting an opening through the lid, including the transition from the planar top of the lid to the depressed opening, and one embodiment of a closure for the opening.

With specific reference to FIG. 4, the lid 32 of the present vessel is provided with a sealing flap 60 comprising an elongated sheet 62 of a liquid-impermeable material such as flexible white matte polyethylene film. This sheet preferably is about 3.8 mil thick. One surface 64 of this sheet is provided with an aggressive permanent pressure sensitive acrylic adhesive backed with a semi-bleached kraft release liner 66. An adhesive thickness of about 0.8–0.9 mil is preferred. In the preferred embodiment, the release liner 66 is in two portions. In use, one portion 68 of the release sheet is removed from one end 70 of the elongated sheet 62 and this end of the sheet 62 is adhesively anchored to the top surface 36 of the lid at a location radially outwardly from the recess 50. The remainder of the adhesive-bearing surface 64 of the sheet remains covered with the release liner until such time as the container is ready for disposal. For disposal purposes, the remainder of the release liner is removed and the adhesive-bearing surface of the sheet 62 is adhesively adhered to the top surface 36 of the body portion 34 of the lid 32 in full covering relationship to the recess 50, thereby effectively sealing both the recess 50 and its associated opening 56 against escape of liquid waste material from the vessel 12 via the opening 56 and its associated recess 50. The adhesive chosen for adhering the sheet 62 to the top surface of the lid is permanent in that it forms a bond with the top surface of the lid which precludes removal of the sheet from the lid without substantial destruction of the sheet. A preferred adhesive exhibits adhesion to acrylic in the range of 65 to 95 oz/in. Therefore, once the sheet is placed in sealing relationship to the recess, the container can not be reused and is ready for disposal, commonly by incineration. Safety in disposal is provided by the planar nature of the sheet 62 and the fact that it lays on the planar top surface 36 of the lid and does not present a protrusion, such as a hinged lid or plug which projects from the plane of the top surface of the lid and is subject to dislodgement, inadvertent opening, or similar incident which would result in the failure of the desired permanent closure of the opening 56 through the lid. This closure feature of the present container is only made possible by reason of the inclusion of a recess in the top surface of the lid, such recess having its major diameter oriented coplanar with the top surface of the lid, so that the closure sheet 62 can be caused to lie fully flat against the top surface of the lid during closure of the recess and its associated opening.

In one embodiment of the present invention, there is provided a length of double-backed adhesive tape 80 having one 81 of its adhesive surfaces adhered to the outer surface 82 of the bottom 14 of the vessel. The exposed surface 86 of the tape is provided with a release sheet 88 which is removable at the time the vessel is placed in use to thereby expose the second adhesive-bearing surface of the tape. This exposed surface of the tape may be adhered to any suitable surface in the theater of operations of the medical personnel to anchor the vessel against inadvertent tipping or overturning of the vessel during its use.

Whereas various materials of construction may be employed in the manufacture of the vessel 12 or the lid 32, in one embodiment, the vessel is vacuum formed from polypropylene of a thickness of about 1/32 inch, thereby providing the desired rigidity to the vessel and resistance to puncture by medical sharps. The lid in this embodiment is vacuum formed from clear PETG, PEG or PVC plastic, preferably PETG to provide a wall thickness of about 25 mil. Each of these materials of the lid or vessel is sufficiently tough as will preclude inadvertent puncture of their wall thickness by surgical sharps, such as needles, etc. In the preferred embodiment, the vessel is colored red in accordance with conventional labeling for receptacles of hazardous waste material. The lid is preferably transparent to permit the visual observation of the contents of the vessel by medical personnel.

Figure 6:
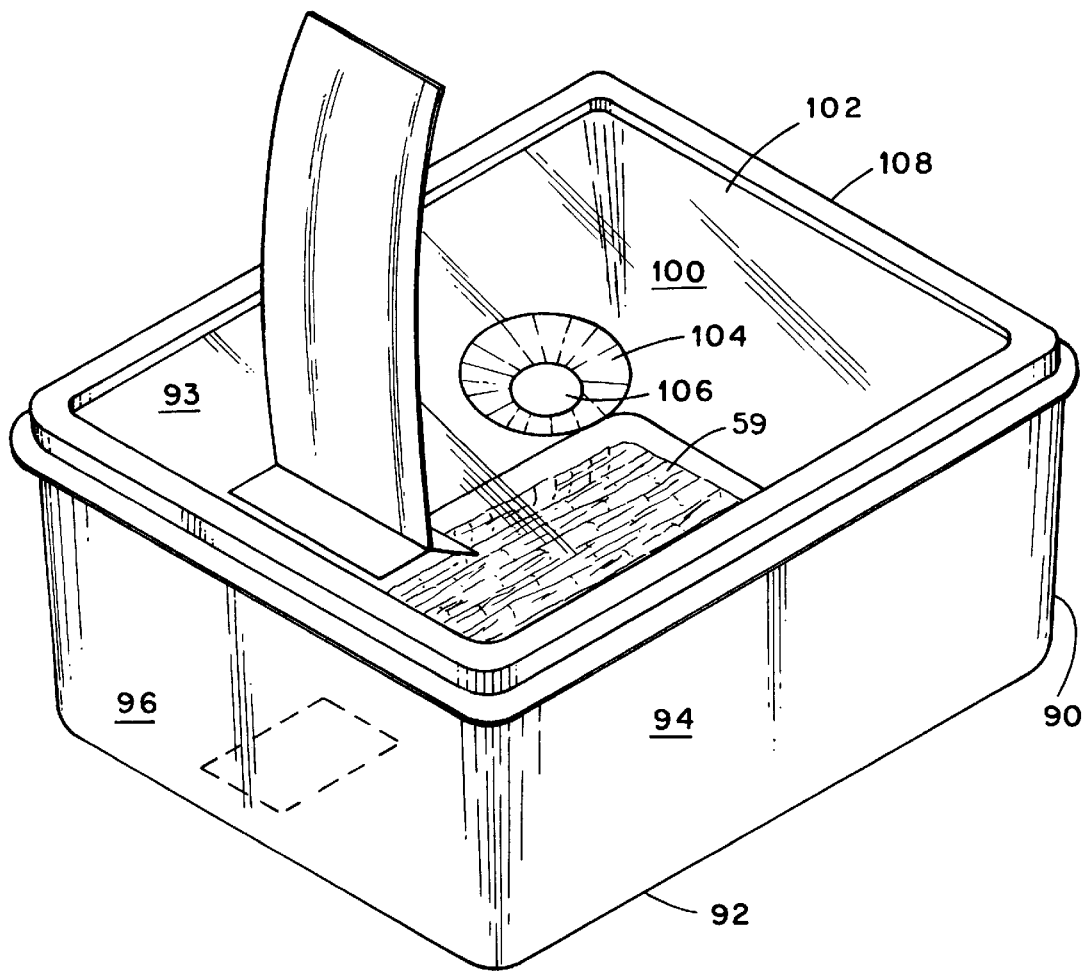

FIG. 6 depicts a further embodiment of a container embodying various of the features of the present invention and in which the vessel 90 is generally rectangular in geometry as defined by a rectangular bottom 92 and upstanding side walls 94,96,98 and 100. The open top of the vessel 90 is covered by a lid 102 having a recess 104 defined generally centrally of the lid and including an opening 106 providing for fluid communication between the interior and exterior of the container. The upper rim 108 of the vessel 90 is substantially identical in configuration and function as the upper rim 22 of the vessel depicted in FIGS. 1 and 5 and described hereinabove as are others of the elements of the depicted container of FIG. 6, the substantive difference being the difference in geometries of the containers of FIGS. 1 and 6.

Whereas the present invention has been described and depicted employing specific features and elements, it will be recognized by one skilled in the art that various modifications and alternatives may be employed without departing from the scope of the invention, which scope is intended to be limited only in accordance with claims appended hereto.

What is claimed:

1. A receptacle for liquid medical wastes dispensable from a carrier having a first portion of a first outer diameter and a second portion of a second outer diameter which is smaller than said first outer diameter and liquid wastes disposed within the carrier are dispensable from the second portion thereof, comprising an open top vessel having a bottom, an integral upstanding wall defining an upper flanged rim, and a lid adapted to cover the open top of the vessel in sealing engagement with the flanged rim, said lid including a substantially flat planar body portion having a flat top surface, a recess of frustoconical geometry depending interiorly of said vessel from said body portion and having a major unobstructed opening and a periphery which resides in a plane which is coincident with the plane occupied by said flat planar body portion, and a minor unobstructed opening disposed interiorly of said vessel relative to said flat planar body portion, and a wall extending between said major and minor openings, said major and minor openings of said recess being in unobstructed fluid communication between the interior and exterior of said vessel, said major opening having a diameter greater than the first outer diameter of carrier whereby both the first and second portions of the carrier may readily pass through said major opening, said minor opening having a diameter less than the second outer diameter of the carrier whereby the second portion of the carrier can pass through said minor opening and said minor opening defines a stop against movement of the first portion of the carrier through said minor opening, whereby the liquid contents of the carrier may be excelled from said second portion of the carrier into said vessel while prohibiting deposit of the carrier into the interior of said vessel, a flexible liquid-impervious closure flap having a flat surface, anchored at one of its ends to said top surface of said body portion of said lid at a spaced apart location relative to said major opening and with its flat surface in position to overlie that portion of said flat top surface of said body portion of said lid, and being of a size sufficient to fully cover said major opening and extend laterally therebeyond to overlie that portion of said flat top surface of said body portion which is laterally immediately contiguous said major opening, a layer of adhesive carried on said flat surface of said flap, said adhesive extending at least to that portion of said flap which extends beyond and overlies said flat top surface of said body portion of said lid immediately contiguous said major opening and exhibiting sufficient adhesion for adhering said flap to that portion of said flat top surface of said body portion which is laterally beyond and immediately contiguous said major opening with said layer of adhesive facing said top surface of said body portion and exhibiting sufficient adhesion for adhering said flap to that portion of said flat top surface of said body portion which is laterally beyond and immediately contiguous said periphery of said major opening in covering and fluid-tight sealing relationship to said major opening.

2. The receptacle of claim 1 and including means for releasably anchoring said receptacle to a supporting surface during its use in a theater of medical operation.

3. The receptacle of claim 1 wherein all components of the receptacle are formed from incineratable materials.

4. The receptacle of claim 1 and including liquid absorptive material disposed interiorly of said vessel.

5. The receptacle of claim 1 wherein said recess is substantially frustoconical in geometry.

6. The receptacle of claim 1 wherein said opening through said lid is of a size sufficient to accept therethrough the distal end of a syringe with minimal clearance between the end of the syringe and the perimeter of said opening.

7. The receptacle of claim 1 wherein the peripheral dimension of said major end of said recess is greater than the periperal dimension of said minor end of said recess so that the wall extending therebetween defines an obtuse angle of between about 140 and about 160 degrees with said body portion of said lid.

8. The receptacle of claim 1 and including a flanged rim on said lid which defines a downwardly opening trough, and said vessel includes an upper rim adapted to be received within said trough in liquid-tight sealing engagement therebetween.

9. The receptacle of claim 1 and including means disposed on said bottom of said vessel for releasably anchoring said vessel to a supporting surface therefor.

10. The receptacle of claim 1 and including a release sheet covering said layer of adhesive and adapted to be removed from said flap for exposure of said layer of adhesive upon removal of said release sheet so that said adhesive on said flat surface of said flap is disposed for its capture between said flat surface of said flap and said flat planar top surface of said body portion of said lid in that portion of said flat top surface which is immediately contiguous to said periphery of said major opening.

* * * * *